United States Patent [19]

Watanabe et al.

[11] 4,008,280

[45] Feb. 15, 1977

[54] PROCESS FOR PRODUCTION OF ACROLEIN

[75] Inventors: Yoshihisa Watanabe; Toshiyuki Sugihara; Kenji Takagi; Makoto Imanari; Naohiro Nojiri, all of Ami, Japan

[73] Assignee: Mitsubishi Petrochemical Company Limited, Tokyo, Japan

[22] Filed: Oct. 1, 1974

[21] Appl. No.: 511,473

Related U.S. Application Data

[63] Continuation of Ser. No. 312,732, Dec. 29, 1971, abandoned.

[30] Foreign Application Priority Data

Dec. 29, 1970 Japan .............................. 50-121235
Dec. 29, 1970 Japan .............................. 50-121238
Dec. 29, 1970 Japan .............................. 50-121239

[52] U.S. Cl. ............................................ 260/604 R
[51] Int. Cl.² ...................................... C07C 45/04
[58] Field of Search ................. 260/604 R; 213/732

[56] References Cited

UNITED STATES PATENTS

| | | |
|---|---|---|
| 3,576,764 | 4/1971 | Yamaguchi et al. ............ 260/604 R |
| 3,679,603 | 7/1972 | Garnish et al. ................. 260/604 R |
| 3,778,386 | 12/1973 | Takenaka et al. .............. 260/604 R |

*Primary Examiner*—James O. Thomas, Jr.
*Assistant Examiner*—W. B. Lone
*Attorney, Agent, or Firm*—Wenderoth, Lind & Ponack

[57] ABSTRACT

For production of acrolein by gas-phase catalytic oxidation of propylene with molecular oxygen, there is used a catalyst containing molybdenum, bismuth, cobalt, nickel, iron, tin, silicon, and a particular borate in a prescribed proportion. Sodium or manganese is employed for formation of the desired borate. For preparation of the catalyst, the borate of each of the metals is preferably supplied in the combined form of a sodium or manganese salt of various boric acids, such as borax, although it may be supplied separately as a boric acid and a decomposable compound of each metal.

10 Claims, No Drawings

PROCESS FOR PRODUCTION OF ACROLEIN

This is a continuation of application Ser. No. 312,732 filed Dec. 29, 1971, now abandoned.

BACKGROUND OF THE INVENTION

This invention relates to a process for production of acrolein, and in particular to a novel and improved process for production of acrolein by gas-phase catalytic oxidation of propylene in which a catalyst of improved composition is utilized.

In production of unsaturated aldehydes by the gas-phase catalytic oxidation of olefins, the use of especially will-prepared catalysts and the selection of most appropriate conditions for the desired reaction are generally importance in order to maintain high conversion of the starting olefins and to keep high selectivity to the desired unsaturated aldehydes and unsaturated carboxylic acids.

There have been already proposed numerous catalysts in order to accomplish these purposes. To give some examples of the catalysts of the class containing molydenum and bismuth in combination, for instance, there are Mo-Bi-P catalysts (as disclosed in Japanese Patent Publication No. 3563/61), Mo-Bi-Fe-P catalysts (Japanese Patent Publication No. 7522/67). In spite of their own advantages, each seems, so far as we know to have some disadvantages in one or more of such points as one-pass yield, selectivity, and durability of the catalyst.

The unsaturated aldehydes produced by the use of such catalysts are often converted to unsaturated carboxylic acids by the ensuing step of oxidation. In this case, the olefin conversion must be kept as high as possible from the economical and industrial point of view. This object has so far been accomplished, wherever the prior catalysts have been used, by such usual procedures as elevating the reaction temperature or increasing their contact time. These procedures, however, accompany a noticeably lowered selectivity of to the unsaturated aldehydes.

SUMMARY OF THE INVENTION

It is an object of the present invention to provide a novel and improved process for the production of acrolein.

Another object of the invention is to provide novel catalysts for particular use in the production of acrolein by gas-phase catalytic exidation of propylene.

According to the present invention, briefly stated, there is provided a process for producing acrolein by catalytic oxidation of propylene with molecular oxygen, which process is characterized by the use of a catalyst of a composition representable by the formula

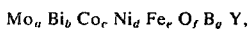

$Mo_a Bi_b Co_c Ni_d Fe_e O_f B_g Y$, wherein: Y is $(X_h Sn_i Si_j)$, $(Na_h, Mn_h)$, $(X_h)$, or $(Xh, Sni)$; X is a metal capable of forming a borate; and subscripts a through j represent numbers of atoms which, when a is fixed at 12, are as follows:

$a = 12$
$b = 0.1$ to $10$
$c$ $20$ to $10$
$d = 0$ to $10$
$c + d = 0.1$ to $15$
$e = 0.05$ to $8$
$f = 25$ of $120$
$g = 0.01$ to $2$
$h = 0$ to $2$
$g + h = 0.01$ to $4$
$i = 0$ to $2$
$j = 0$ to $40$

DETAILED DESCRIPTION

It has been confirmed by the present inventors that, for the purpose of longer life and a higher selectivity, catalysts must be used at as low a temperature as possible. Further efforts expended by the inventors to discover catalysts which will provide unsaturated aldehydes with high selectivity while a high degree of olefin conversion is maintained have revealed that the use of catalysts containing the oxides of molybdenum, bismuth, cobalt, nickel, tin and iron, and a small amount of a borate in a specific ration leads to a sufficiently high space-time yield under comparatively moderate conditions of reaction. Such catalysts also proved to have an extremely high degree of selectivity with respect to unsaturated aldehydes. The present invention is based on these findings.

Accordingly, one of the features of this invention resides in the use of catalysts containing the oxides of molybdenum, bismuth, cobalt, nickel, tin and iron, and a small amount of a borate, for the production of acrolein (and acrylic acid) through gas-phase catalytic oxidation of propylene with molecular oxygen.

More specifically, a catalyst used for the production of acrolein in accordance with this invention contains molybdenum, bismuth, cobalt, nickel, iron, tin, and silicon in such an atomic ratio that, if the number of molybdenum atoms is set to 12, bismuth = 0.1 to less than 10, cobalt = 0 to 10, nickel = 0 to 10, the sum of nickel and cobalt = 0.1 to 15, iron = 0.05 to 8, tin = 0 to 2, and silicon = to 40 (preferably 3 to 25). A catalyst within this range is found to exhibit particularly excellent performance characteristics when further provided with a specific borate by a quantity in the range of 0.01 to 2 in terms of the number of boron atoms relative to the above determined number of molybdenum atoms.

It is important that the borate to be added to the catalyst of the above specified composition be either a sodium or manganese/salt. Potassium borate, for example, does not provide the desired results, as demonstrated later in Comparison D1. It is noteworthy, however, that the same potassium which does not show satisfactory results when supplied in the form of a borate does exhibit considerably favorable results when supplied in the form of a phosphate, as explained in Comparison D2.

The catalyst used in the present invention, when defined in the broadest sense, has the following composition:

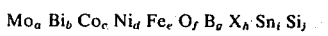

$Mo_a Bi_b Co_c Ni_d Fe_e O_f B_g X_h Sn_i Si_j$ in which X is a metal capable of forming a borate and to be selected from the group consisting of sodium and manganese, and in which a to j denote the numbers of atoms of the respective elements. If "a" is set to 12, the values of these letters will be:

$a = 12$
$b = 0.1$ to $10$
$c = 0$ to $10$
$d = 0$ to $10$
$c + d = 0.1$ to $15$ $e = 0.05$ to 8
$f = 25$ to 120
$g = 0.01$ to 2
$h = 0$ to 2
$g + h = 0.01$ to 4
$i = 0$ to 2
$j = 0$ to 40

Catalysts satisfying the above conditions and thus employable for the production of acrolein in accordance with this invention are classificable into several classes, as hereinafter described in detail.

CLASS A

A catalyst in this first class contains molybdenum, bismuth, nickel, and/or cobalt, and iron in such an atomic ratio that if the number of molybdenum atoms is set to 12, bismuth = 4 to 7, iron = 0.05 to 0.5, cobalt = o to 10 (preferably 1 to 7.5), nickel = o to 10 (preferably 1 to 7.5), and the sum of cobalt and nickel contents = 0.1 to 15 (preferably 1.5 to 10). The desired favorable performance characteristics are realized when this catalyst is further provided with a borate of sodium or manganese by a quantity in the range of 0.01 to 2 (preferably 0.05 to 1.5) in terms of the atoms of boron, and with sodium or manganese by a quantity in the range of 0.01 to 2.

A catalyst containing molybdenum, bismuth, nickel, iron, and silicon in the atomic ratio of 12 : 5 : 4 : 0.4 : 12.5 and supported in concentration of 30 percent by porous d-alumina carrier, for example, exhibits, at a reaction temperature of about 380° C, 88.8 percent of propylene conversion and 89.3 percent of the total selectivity for acrolein and acrylic acid. When further provided with borax (sodium tetraborate) by a quantity equal to 0.1 in terms of the number of boron atoms, this catalyst exhibits, at a considerably reduced reaction temperature of about 350° C, 91.3 percent of propylene conversion and 90.0 percent of selectivity for the sum of acrolein and acrylic acid. Catalysts having compositions out of the above defined scope, like those not provided with the borates, indicated no such favorable results.

CLASS B

A catalyst in this Class B contains molybdenum, bismuth, cobalt, nickel, iron, tin, silicon, and oxygen in such an atomic ratio that if the number of molybdenum atoms is set to 12, bismuth = 0.1 to less than 4, cobalt = 0 to 10, nickel = 0 to 10, the sum of nickel and cobalt contents = 1 to 15, iron = 0.1 to 2.5, tin = 0 to 2, silicon = 0.5 to 40 (preferably 3 to 25), and oxygen = 30 to 120. Particularly favorable performance characteristics are demonstrated by this catalyst when the same is additionally provided with a borate by a quantity in the range of 0.01 to 2 in terms of the number of boron atoms.

The oxidation reaction of propylene was conducted, by way of experiment, with a catalyst containing molybdenum, bismuth, cobalt, nickel, iron, silicon, and borax (sodium tetraborate) as the desired borate in the atomic ratio of 12 : 1 : 4 : 4 : 0.4 : 6 : 0.1 (the borax content being given in terms of the atomic of boron) and 20 percent supported by porous d-alumina carrier. At a reaction temperature of 350° C, 97.5 percent of propylene conversion, 95.4 percent of the total selectivity for acrolein and acrylic acid, and 93 percent of the one-pass yield from propylene were realized. Catalysts containing the above listed elements in a ratio out of the scope of this Class or lacking some of the elements indicated no such satisfactory results (rever also to Comparisons given later in this specification).

More specifically, catalysts belonging to this Class D may be subclassified as follows according to the ratios of their contents:

$$Mo_a\ Bi_b\ Co_c\ Ni_d\ Fe_e\ O_f\ B_g\ X_h\ Sn_i\ Si_j$$

1. $a = 12$, $b = 0.1$ to less than 4. $c = 0$ to 2. $d = 0$ to 2. $c + d = 1$ to less than 2. $e = 0.1$ to less than 0.5. $f = 30$ to 120. $g = 0$ to 2. $h = 0$ to 2. $g + h = 0.01$ to 4. $i = 0$. $j = 0.5$ to 40.
2. $a = 12$. $b = 0.1$ to 4 (preferably 0.5 to 3). $c = 0$ to 10. $d = 0$ to 10. $c + d = 2$ to 15. $e = 0.1$ to less than 0.5. $f = 30$ to 120. $g = 0$ to 2. $h = 0$ to 2. $g + h = 0.01$ to 4. $i = 0$. $j = 0.5$ to 40.
3. $a = 12$. $b = 0.1$ to less than 4 (preferably 0.5 to 3). $c = 0$ to 10. $d = 0$ to 10. $c + d = 1$ to 15. $e = 0.5$ to 2.5. $f = 30$ to 120. $g = 0$ to 2. $h = 0$ to 2. $g + h = 0.01$ to 4. $i = 0$. $j = 0.5$ to 40.
4. $a = 12$. $b = 0.1$ to less than 4 (preferably 0.5 to 3). $c = 0$ to 10. $d = 0$ to 10. $c + d = 1$ to 15. $e = 0.1$ to 2.5. $f = 30$ to 120. $g = 0$ to 2. $h = 0$ to 2. $g + h = 0.01$ to 4. $i = $ less than 2. $j = 0.5$ to 40.

Catalysts of subclass (2) can greatly improve the percentages of conversion and selectivity, whereas catalysts of subclass (4) are effective to improve conversion at low temperatures.

CLASS C

A catalyst in this class contains molybdenum, bismuth, cobalt, nickel, iron, and tin in such an atomic ratio that if the number of molybdebum atoms is set to 12, bismuth = 4 to less than 7, cobalt = 0 to 10 (preferably 0 to 7.5), nickel = 0 to 10 (preferably 0 to 7.5), the sum of cobalt and nickel contents = 1 to 15 (preferably 1 to 10), iron = 0.1 to 8 (preferably 0.5 to 3), and tin = 0.1 to less than 2. Further improved reactivity and selectivity will be exhibited by this catalyst if it is additionally provided with a borate of sodium or manganese by a quantity in the range of 0.01 to 2 in terms of the number of boron atoms.

For instance, a catalyst containing molybdenum, bismuth, nickel, iron, tin, and borax (sodium tetraborate) in the atomic ratio of 12 : 5 : 4 : 0. 4 : 0.2 : 0.1 (the borax content being given in terms of the number of boron atoms) and 31.6 percent supported by porous d-alumina carrier was employed for the oxidation reaction of propylene. At a reaction temperature of about 350° C, 95.6 percent of propylene conversion and 88.9 percent of the total one-pass yield of acrolein and acrylic acid were exhibited. These results are considerably better than those (77.3 percent of propylene conversion and 72.0 percent of the total one-pass yield of acrolein and acrylic acid) exhibited under the same reaction conditions by a catalyst containing molybdenum, bismuth, nickel, and iron in the atomic ratio of 12 : 5 : 4 : 0.4, or than those (88.7 percent of propylene conversion and 81.5 percet of the total one-pass yield of acrolein and acrylic acid) indicated by a catalyst containing borax by a quantity of 0.1 in terms of the atomic number of boron in addition to the listed contents of the precedingly mentioned catalyst. Also, no truly satisfactory results were exhibited by catalysts containing the elements of this Class E in proportions out of the scope of the Class, as described later in several Comparisons.

Although the exact structure of the various catalysts of this invention is not necessarily ascertained, it seems that the oxides of molybdenum, cobalt, nickel, bismuth, etc., as well as boron or a metal such as sodium or manganese capable of forming a borate are combined into complex mixtures or compounds to form excellent catalyst species. Particularly, the presence of boron and/or sodium or manganese is indispensable in the catalysts of this invention, in order to realize the greatly improved selectivity with a high percentage of conversion.

Japanese Patent Publication Nos. 6245/69 and 6246/69, for example, disclose catalysts containing molybdenum, bismuth, iron, nickel, cobalt, phosphorus and/or arsenic. The proposedly most excellent one of the prior catalysts of this class, which contains molybdenum, bismuth, iron, cobalt, nickel, phosphorus and silicon in the atomic ratio of 12 : 1 : 1 : 4 : 4.5 : 0.08 : 12.5 as disclosed in Example 1 of Japanese Patent Publication No. 6245/69, and which is supported by $\alpha$-alumina, was used by the present inventors for the air oxidation of propylene. This prior catalyst exhibited 90.6 percent of total selectivity for acrolein and acrylic acid at 90 percent of propylene conversion, and 88.5 percent of total selectivity for acrolein and acrylic acid at 97 percent of propylene conversion.

Contrastively, a catalyst containing molybdenum, bismuth, iron, cobalt, nickel, borax and silicon in the atomic ratio of 12 : 1 : 1 : r : 4.5 : 0.1 : 12.5 (the borax content being given in terms of the atomic of boron) in accordance with the present invention and which is supported by $\alpha$-alumina was subjected to the same reaction is indicate 96.3 percent of total selectivity for acrolein and acrylic acid at 90 percent of propylene conversion, and 95.0 percent of total selectivity for acrolein and acrylic acid at 97 percent of propylene conversion.

These two experiments were further compared as to selectivity for carbon monoxide and carbon dioxide produced as a result of complete oxidation. While 9.2 percent of total selectivity for carbon monoxide and carbon dioxide was indicated at 97 percent of propylene conversion by the former experiment, in which was used the prior catalyst, only 3.7 percent was exhibited by the latter experiment using the catalyst of this invention. This seems to demonstrate the fact that the addition of a borate to the known catalyst provides a completely different catalyst having completely different active species.

The preparation of a catalyst in accordance with the present invention may be effected by any desired process ordinarily adopted for preparation of comparable oxide catalysts, although due consideration must be paid for the specified proportion of its contents. Usually, the compounds of specified metals which are thermally decomposable into oxides, or the compounds of the metals which are converted into oxides when heated in an atmosphere of molecular oxygen, may be calcined. A group of such precursor compounds are soluble, usually in water. In this case, their solutions may be soaked through suitable carrier materials and then dried. Another group of the precursor compounds are insoluble, usually in water, in which case they may be prepared by precipitation as a result of reaction their soluble precursors and an insolubizing or precipitating agent either in the presence or absence of carrier materials.

Molybdenum may be prepared from such materials as molybdic acid or ammonium molybdate; bismuth from such materials as bismuth nitrate or basic bismuth nitrate; and/iron from such materials as iron nitrate and iron oxalate. Cobalt and nickel may be respectively prepared from salts such as oxalates and nitrates which can be calcined into oxides, or from oxides or hydroxides. Silicon may be prepared from silicon oxides commercially available in the form of granules, gel, or sol, under trade names such as "Aerosil" (of Nippon Aerosil K.K.), "Carplex" (Shionogi Seiyaku K.K.), and "Snowtex" (Nisson Kagaku K.K.). Alternatively various silicon compounds may be used which yield silicon oxides when baked or fired. Tin, which is added to the catalysts of this invention as required, can be prepared from stannous chloride, stannic chloride, and so forth.

Boron, and sodium or borate, which are very important elements of the various catalysts herein disclosed, may be prepared respectively from boric acid and the decomposable compound of each metal, such as hydroxides, oxides, nitrated, and organic salts. Since boron and one of the metals should preferably exist-/together, they may be combinedly supplied in the form of a borate such as, for example, a sodium or manganese salt of metaboric or tetraboric acid. It is possible, of course, to supply boric acid and a decomposable compound of each metal separately.

A carrier which is employable as desired may preferably be silicon carbide, $\alpha$-alumina, or the like, to prevent combustion at the time of reaction hereinafter to be described.

For actual preparation of a catalyst in accordance with this invention, an aqueous solution of molybdenum may be first prepared, to which are then added the suitable compounds of bismuth, iron, nickel and/or cobalt, and, if desired, tin. The slurried suspension thus formed is further supplied with a borate and a prescribed amount of silicon/oxide. After well dispersing the elements in the suspension, it may be dried. The thus-formed cake is thermally decomposed, at a temperature ranging between 270° C and 500° C, into the desired oxides. These are then formed into a desired shape by any such prior procedure as extrusion and compression molding. After being further heat treated in a temperature range of from about 450° C to 650° C, the product is made ready for use as a catalyst.

Desirably, however, the oxides formed by the aforesaid thermal decomposition of the cake are sufficiently pulverized into fine particles. Supported by a quantity in the range of from 10 to 40 percent (preferably from 20 to 35 percent by weight by such an inactive, porous carrier as silicon carbide or $\alpha$-alumina, these particles are thermally treated in the temperature range of from about 450° C to 650° C. In this manner, the catalyst is found to exhinit still more improved performance characteristics, especially selectivity. It must also be noted that the performance of the catalyst is affected according to the temperature of the final heat treatment. Particularly favorable selectivity and yield will be indicated if the catalyst is heated in the temperature range of from about 500° C to 600° C.

Although the catalysts of this invention may be used on a stationary bed, they can be used on a moving or fluidized bed, too.

The catalytic oxidation according to the process of this invention is carried out in the temperature range of from about 250° to 450° C, preferably from about 250° to 400° C, and in the pressure range of from about 0.5 to 10 atmospheric pressures. A gaseous mixture for use in the reaction may be of any desired composition, but it should preferably contain propylene in a concentration of from 2 to 10 mol percent and molecular oxygen in a concentration of from 5 to 30 mol percent, and should be prepared without the limit of inflammability. While oxygen of commercially available purity may be used as the molecular oxygen, the use of air is more economical. A mixture of oxygen and an inactive gas, such as steam and oxygen of commerical purity, or oxygen and carbon dioxide, is of course employable as required.

In order to realize the above specified concentrations of propylene and molecular oxygen, a/gaseous mixture such as, for example, that of propylene and oxygen or of propylene and air must be diluted with an inactive gas such as nitrogen, carbon dioxide, argon, steam, and any other gas which is inactive under specified conditions of the reaction. The use of steam as part of such inactive gas, usually in the range of from 2 to 55 mol percent, is preferable in order to prevent complete combustion and to remove undesired heat. A contact time of the gaseous mixture with a selected catalyst of this invention may range from about 0.2 to 20 seconds, preferably from about 2 to 15 seconds, at a normal pressure, although this is subject to variation according to the pressure and temperature conditions of the reaction.

The nature, utility, and advantages of this invention will be made more apparent by the following description of Examples, together with Comparisons with the prior art.

EXAMPLES A1 AND A2

Catalysts containing different borates were prepared as hereinafter described. Fifty-three grams of ammonium molybdate was dissolved in 75 milliliters of water. Separately, 4 grams of iron nitrate and 29.1 grams of nickel nitrate were dissolved in water. Together with 60.5 grams of bismuth nitrate dissolved in distilled water which had been rendered acidic with nitric acid, the aqueous solution of the iron and nickel nitrates were added to the aforesaid aqueous solution of ammonium molybdate.

The thus-obtained solution was admixed with 0.24 gram of borax dissolved in 10 milliliters of water and with 9.4 grams of finely granulated silica (a commercially available product known by the trade name "Carplex"). The admixture was then evaporated to dryness and was baked at 300° C for one hour into a powdered oxide mixture. Forty grams of $\alpha$-alumina in the form of porous balls each with a diameter of about 4 millimeters (a commercially available product of Fujimi Kenmazai Kogyo K.K., of Japan) was added to 21.6 grams of the powdered oxide, and the resultant product was heat-treatedor baked at 500° C for three hours thereby to produce a catalyst consisting of the oxide mixture supported on the $\alpha$-alumina balls. The mentioned 0.24 gram of borax is replaceable with 2.2 grams of manganess borate without any alteration in the other details of procedure described in the foregoing.

Twenty cubic centimeters each of the catalysts thus prepared was charged into a reactor tube of stainless steel with an ineder diameter of 15 millimeters. A gaseous mixture of 4.5 percent of propylene, 53 percent of air, and 42.5 percent of steam was contacted therewith for 9 seconds at a reaction temperature of 350° C. The results of the reaction are given in Table A-1 below.

Table A-1

| Example No. | Catalyst Composition | | | | | | Reaction Temperature, ° C | $C_3$ Conversion % | ACR Selectivity, % | AA Selectivity, % | ACR+AA One pass Yield, % |
|---|---|---|---|---|---|---|---|---|---|---|---|
| | Mo | Bi | Fe | Ni | Si | Borate (B) | | | | | |
| A1 | 12 | 5 | 0.4 | 4 | 12.5 | $Na_2B_4O_7 10H_2$) 0.1 | 350 | 91.3 | 77.2 | 12.8 | 82.1 |
| A2 | 12 | 5 | 0.4 | 4 | 6.25 | $MnB_4O_7 8H_2O$ 0.1 | 350 | 94.3 | 73.4 | 18.5 | 86.7 |

Notes:
1) $C_3$ = Propylene. ACR = Acrolein. AA = Acrylic Acid.
2) Acetaldehyde, acetic acid, carbon monoxide, and carbon dioxide are also produced secondarily.

EXAMPLES A3 TO A11

Catalysts given herein as examples A3 to A11, in which only the percentages of bismuth, cobalt, nickel, silica, and borax contents are varied, were prepared by substantially the same way as Examples A1 and A2. Also the same experiment as that set forth in description of the preceding Examples was conducted to obtain the results tabulated in the following:

Table 2 A-2

| Example No. | Catalyst Composition | | | | | | Borax (as "B") | Reaction Temperature ° C | $C_3$ Conversion % | ACR Selectivity % | AA Selectivity, % | ACR + AA One-pass Yield, % |
|---|---|---|---|---|---|---|---|---|---|---|---|---|
| | Mo | Bi | Co | Ni | Fe | Si | | | | | | |
| A 3 | 12 | 5 | 6 | | 0.4 | 6.25 | 0.1 | 350 | 81.4 | 82.3 | 8.6 | 74.0 |
| A 4 | 12 | 5 | 6 | | 0.4 | 6.25 | 0.1 | 350 | 94.0 | 81.7 | 7.3 | 83.7 |
| A15 | 12 | 4 | | 4 | 0.4 | 6.25 | 0.1 | 350 | 93.9 | 75.6 | 11.4 | 81.7 |
| A16 | 12 | 7 | | 4 | 0.4 | 6.25 | 0.1 | 380 | 90.7 | 76.7 | 7.3 | 76.2 |
| A17 | 12 | 5 | | 4 | 0.4 | 6.25 | 0.2 | 350 | 91.0 | 79.1 | 10.4 | 81.4 |
| A18 | 12 | 5 | | 4 | 0.4 | 12.5 | 1 | 350 | 91.8 | 75.8 | 13.1 | 81.6 |
| A 9 | 12 | 5 | 4 | | 0.4 | 12.5 | 0.1 | 380 | 95.2 | 74.4 | 13.3 | 83.5 |
| A10 | 12 | 5 | 1 | 3 | 0.4 | 12.5 | 0.2 | 350 | 91.5 | 77.9 | 11.9 | 82.2 |
| A11 | 12 | 5 | 2 | 2 | 0.4 | 12.5 | 0.1 | 350 | 90.0 | 81.7 | 8.8 | 81.5 |

EXAMPLES A12 AND A13

The catalyst of Example A1 was subjected to different reaction temperatures given in the following Table A-3:

Table A-3

| Example No. | Reaction Temperature, °C | C₃ Conversion, % | ACR Selectivity, % | AA Selectivity, % | ACR+AA One-pass Yield, % |
|---|---|---|---|---|---|
| A 12 | 380 | 95.7 | 69.9 | 18.4 | 84.5 |
| A 13 | 410 | 98.0 | 55.4 | 24.4 | 78.2 |

EXAMPLES A14 TO A17

A catalyst having the same composition as that of Example A11 was subjected to different final baking temperatures as set forth in the following table A-4:

Table A-4

| Example No. | Firing Temperature, °C | Reaction Temperature, °C | C₃ Conversion, % | ACR Selectivity, % | AA Selectivity, % | ACR+AA One-pass Yield, % |
|---|---|---|---|---|---|---|
| A14 | 450 | 350 | 91.9 | 79.9 | 10.2 | 82.8 |
| A15 | 500 | 350 | 85.5 | 82.3 | 8.5 | 77.6 |
| A16 | 550 | 350 | 90.6 | 83.8 | 7.1 | 82.4 |
| A17 | 600 | 350 | 75.4 | 83.6 | 7.3 | 68.5 |

EXAMPLE A18

Five milliliters of a catalyst having the same composition as that of Example A1 was reacted with the gaseous mixture referred to in the description of the same Example A1, at a reaction temperature of 380° C and with a contact time of 2.3 seconds. The results were:
Propylene conversion = 55.2 percent.
Acrolein selectivity = 86.0 percent.
Acrylic acid selectivity = 5.8 percent.

EXAMPLE A19

The same catalyst and the same conditions of reaction as those set forth in the preceding Example A18, except for the use of a/gaseous mixture consisting of 9 percent of propylene, 51 percent of air, and 40 percent of steam, were employed to conduct the same experiment. The results are given below:
Propylene conversion = 48.2 percent.
Acrolein selectivity 32 88.5 percent.
Acrylic acid selectivity = 3.5 percent.

EXAMPLE A20 TO A22

Seven hundred milliliters of a catalyst having the same composition as that of Example A7 was charged into a pressure-resisting reactor tube of stainless steel with an inner diameter of 27 millimeters. A gaseous mixture consisting of 5 percent of propylene, 55 percent of air, and 40 percent of steam was employed for reaction with the catalyst, with a contact time of 9 seconds and at various pressure and temperatures. The results are given in Table A-5 below.

EXAMPLE A23

The powder which was prepared in accordance with the process of Example A1 and which was carried through the step of thermal decomposition at 300° C for one hour was formed into a columnar shape with a diameter of 4 millimeters by means of a tabletting machine. After being baked at 500° C for 3 hours, 30 milliliters of the catalyst was introduced into a reactor tube of stainless steel with an inner diameter of 20 millimeters. The specimen was then treated under the same conditions of reaction as those of Example A1 except that the reaction temperature was changed to 290° C. The results were:
Propylene conversion = 80.5 percent.
Acrolein selectivity = 81.7 percent.
Acrylic acid selectivity = 5.7 percent.
(AA + ACR) one-pass yield = 70.3 percent.
Acetaldehyde, acetic acid, carbon monoxide, and carbon dioxide were also produced secondarily.

COMPARISON A1

Except for the absence of borax, a catalyst was prepared in exact accordance with Example A1, and was subjected to a reaction similar to that set forth in description of the same Example, only with the reaction temperature elevated to 380° C. Of the total propylene content supplied, 88.8 percent reacted, of which 77.9 percent was converted to acrylein and 11.4 percent to acrylic acid. Compared with the catalyst of Example A1, this specimen given by way of Comparison A1 obviously requires a higher temperature to attain a similar degree of activity.

COMPARISONS A2 to A3

Several catalysts having compositions out of the scope of this invention were prepared in substantial accordance with the process of Example A1 and was subjected to the same reaction as that Example. The results are summarized in Table A-6.

Table A-5

| Example No. | Reaction Pressure, atm. | Reaction Temperature, °C | C₃ Conversion, % | ACR Selectivity, % | AA Selectivity, % | ACR+AA One-pass Yield, % |
|---|---|---|---|---|---|---|
| A20 | 1 | 360 | 88.1 | 79.4 | 12.2 | 80.7 |
| A21 | 2 | 380 | 86.9 | 74.9 | 13.9 | 77.0 |
| A22 | 3 | 380 | 85.6 | 72.9 | 13.9 | 74.3 |

Table A-6

| Comparison No. | Catalyst Composition | | | | | | Borax (as "B") | Reaction Temperature, °C | C₃ Conversion % | ACR Selectivity, % | AA Selectivity, % | ACR+AA One-pass yield % |
|---|---|---|---|---|---|---|---|---|---|---|---|---|
| | Mo | bi | Co | Ni | Fe | Si | | | | | | |
| A 2 | 12 | 5 | | 4 | 5 | 6.3 | 0.1 | 350 | 90.3 | 65.9 | 5.4 | 64.4 |
| A 3 | 12 | 1 | 4 | 4.5 | 3 | 12.5 | 0.1 | 350 | 81.4 | 70.2 | 4.6 | 60.9 |

EXAMPLES B2 TO B12

Several catalysts of varied compositions, all within the range 600° C, was employed to effect the oxidation reaction of propylene under exactly the some conditions as those in Example C2. The results were:
Propylene conversion = 49.5 percent.
(AA + ACR) selectivity = 92.5 percent.
(AA + ACR) one-pass yield = 45.8 percent.

EXAMPLE B1

Fifty-three grams of ammonium paramolybdate [$(NH_4)_6Mo_7O_{24} \cdot 4H_2O$] was dissolved in 75 milliliters of lukewarm water, and 9.4 grams of finely granulated silica (a commercially available product known by the trade name "Aerosil 200") was sufficiently dispersed in the aqueous solution to provide a first solution.

Separately, 12.1 grams of bismuth nitrate ]$Bi(NO_3)_3 \cdot 5H_2O$] was dissolved in a solution consisting of 3 milliliters of concentrated nitric acid and 60 milliliters of distilled water. Further dissolved in this solution were 29.1 grams of cobalt nitrate [$Co(NO_3)_2 \cdot 6H_2O$], 32.7 grams of nickel nitrate [$Ni(NO_3)_2 \cdot 6H_2O$], and 4 grams of ferric nitrate [$Fe(NO_3)_3 \cdot 9H_2O$]. A second solution was thus prepared.

A third solution was further prepared by dissolving 0.24 gram of sodium tetraborate ($Na_2B_4O_7 \cdot 10H_2O$) in 10 milliliters of distilled water.

While being agitated sufficiently, the first solution was gradually admixed first with the second solution and then with the third solution. While stirring the precipitates formed in the resultant solution, this solution was evaporated to dryness. The thus-formed cake was decomposed for one hour in an electric furnace heated to a temperature of 300° C, and for another one hour at 400° C. The wet milling of 21.5 grams of the above obtained mixture of oxides, plus a small quantity of distilled water, was effected to a sufficient degree in a kneading machine. The product was then made to be carried by 40 grams of α-alumina in the form of porous balls each with a diameter of about 5 millimeters (manufactured by Fujimi Kenmazai Kogyo K.K.), and was baked at 530° C for 3 hours in air within an electric furnace.

The catalyst thus prepared, which constituted 22 percent by weight of the total product, proved to contain molybdenum, bismuth, iron, cobalt, nickel, silicon, boron, and sodium in the atomic ratio of 12 : 1 : 0.4 : 4 : 4.5 : 6.3 : 0.1 : 0.05.

Some 20 milliliters of the catalyst was filled in a reactor tube of stainless steel with an inner diameter of 15.0 millimeters. A gaseous mixture consisting of 4.5 percent by volume of propylene, 53 percent by volume of air, and 42.5 percent by volume of steam was subjected to reaction on the sample catalyst at a temperature of 350° C ans a contact time of 9 seconds. The results were as follows:
Propylene conversion = 99.4 percent.
Acrolein selectivity = 81.4 percent.
Acrylic acid selectivity = 13.6 percent.
(AA + ACR) one-pass yield = 94.4 percent.
Acetaldehyde, acetic acid, carbon monoxide, and carbon dioxide were also produced a little as by-products.

EXAMPLE B2

The catalyst of Example B1 was used for reaction of the same gaseous mixture and under the same conditions as in Example B1, only with the reaction temperature lowered to about 320° C. The results were:
Propylene conversion = 95.7 percent.
Acrolein selectivity = 89.7 percent.
Acrylic acid selectivity = 6.4 percent.
(AA + ACR) one-pass yield = 91.9 percent.
Acetaldehyde, acetic acid, carbon monoxide, and carbon dioxide were also yielded as by-products.

EXAMPLE B3

A catalyst was produced in substantial accordance with Example B1, only with the mentioned 9.4 grams of finely gradulated silica substituted with 92 grams of silica sol containing 20 percent of silicon dioxide ("Snowtex N").

The salts used for production of this catalyst are enumerated below with their weights:
Ammonium paramolybdate = 53 grams.
Bismuth nitrate = 12.1 grams.
Iron nitrate = 10.1 grams.
Cobalt nitrate = 58.2 grams.
Sodium tetraborate = 0.24 gram.
The catalyst thus produced, which constituted 33.0 percent by weight of the total product, proved to contain molybdenum, bismuth, iron, cobalt, silicon, boron, and sodium in the atomic ratio of 12 : 1 : 1 : 8 : 12.5 : 0.1 : 0.05.

This catalyst was subjected to the same reaction as that described in Example B1, with the results shown in the following:
Propylene conversion = 98.9 percent.
Acrolein selectivity = 79.0 percent.
Acrylic acid selectivity = 13.7 percent.
(AA + ACR) one-pass yield = 91.9 percent.
There were additionally yielded small quantities of such by-products as acetaldehyde, acetic acid, carbon monoxide, and carbon dioxide.

EXAMPLE B4

Fifty-three grams of ammonium paramolybdate [$(NH_4)_6Mo_7O_{24} \cdot 4H_2O$] was dissolved in 75 milliliters of hot distilled water. While being sufficiently agitated, this solution was successively admixed with (1) nickel nitrate [$Ni(NO_3)_2 \cdot 6H_2O$] dissolved in 30 milliliters of distilled water, (2) 29.1 grams of cobalt nitrate Co(-$NO_3$)$_2 \cdot 6H_2O$ dissolved in 30 milliliters of distilled water, (3) 4 grams of iron nitrate [$Fe(NO_3)_3 \cdot 9H_2O$] dissolved in 10 milliliters of distilled water, (4) 12.1 grams of bismuth nitrate dissolved in an aqueous solution containing 1.2 milliliters of concentrated nitric acid, (5) 0.24 gram of sodium tetraborate ($Na_2B_4O_7 \cdot 10H_2O$)

dissolved in 10 milliliters of water, and (6) 92 grams of silica sol containing 20 per cent of silicon dioxide ("Snowtex N").

While the precipitates formed in the resultant solution were being sufficiently stirred, this solution was evaporated to dryness. The thus-formed cake was decomposed into oxide by being heated in an electric furnace at 300° C for one hour. Of the powder thus produced, 21. t grams was sufficiently milled in a kneading machine with a small quantity of water added thereto. The product was then sufficiently attached to 40 grams of α-alumina carrier in the form of porous balls each with a diameter of 4.6 millimeters (a commercially available product known by the trade name "Macroport" of Norton Corp.) and was colcined at 500° C for 3 hours in air.

The resultantly obtained catalyst, which constituted about 26.8 per cent by weight of the total product, proved to contain molybdenum, cobalt, nickel, iron, silicon, boron, and sodium in the atomic ratio of 12 : 1 : 4 : 4.5 : 0.4 : 12.5 : 0.1 : 0.05.

Twenty milliliters of this catalyst was charged into the same reactor tube as that of Example B1 and was made to react, at a temperature of 350° C and for a contact time of 9 seconds, with a gaseous mixture consisting of 4.5 percent by volume of propylene, 53 percent by volume of air, and 42.5 percent volume of steam. The results are demonstrated below:

Propylene conversion = 97.9 percent.
Acrolein selectivity = 81.8 percent.
Acrylic acid selectivity = 11.1 percent.
(AA + ACR) one-paaa yield = 90.9 percent.
Acetaldehyde, acetic acid, carbon monoxide, and carbon dioxide were also produced a little.

means of a tabletting machine. The product was then baked at 500° C for 3 hours in air.

Five milliliters of the catalyst thus prepared was subjected to reaction, at 350° C and for a contact time of 2.3 seconds, with the gaseous mixture having the same composition as that of Example B4. The following results were obtained:

Propylene conversion = 93.5 percent.
Acrolein selectivity = 55.8 percent.
Acrylic acid selectivity = 27.9 percent.
(AA + ACR) one-pass yield = 78.3 percent.
By-products such as acetaldehyde, acetic acid, carbon monoxide, and carbon dioxide were also produced.

EXAMPLES B6 TO B17

Various catalysts having compositions within the scope of this invention were produced in substantial accordance with Example B4 and were each used for reaction of the same gaseous mixture and under the same conditions as in Example D4. The porous α-alumina carrier was set to 28 percent in each and all of Examples B6 to B17. The results of the respective reactions were summarized in the following Table B-1.

Table B-1

| Example No. | Catalyst Composition | | | | | Borax (asB) | Reaction Temperature, °C | $C_3$ Conversion % | ACR Selectivity, % | AA Selectivity, % | ACR+AA One-pass Yield, % |
| --- | --- | --- | --- | --- | --- | --- | --- | --- | --- | --- | --- |
| | Bi | Fe | Ni | Co | Si | | | | | | |
| B 6 | 0.5 | 0.4 | 4.5 | 4 | 6.3 | 0.1 | 350 | 99.1 | 82.1 | 13.1 | 94.3 |
| B 7 | 2 | 0.4 | — | 8 | 6.3 | 0.1 | 350 | 91.2 | 82.0 | 8.7 | 82.7 |
| B 8 | 1 | 1 | — | 1 | 12.5 | 0.1 | 350 | 99.5 | 72.3 | 14.8 | 86.7 |
| B 9 | 1 | 0.4 | 4 | — | 6.3 | 0.1 | 350 | 98.9 | 71.8 | 16.6 | 87.4 |
| B10 | 1 | 0.4 | 8 | — | 12.5 | 0.1 | 350 | 98.3 | 69.7 | 16.6 | 84.8 |
| B11 | 1 | 0.4 | 2 | 6.5 | 12.5 | 0.1 | 350 | 96.8 | 67.1 | 20.1 | 84.4 |
| B12 | 1 | 0.4 | — | 10 | 6.3 | 0.1 | 350 | 93.6 | 84.1 | 6.2 | 84.5 |
| B13 | 1 | 0.4 | 4.9 | 5 | 6 | 0.2 | 350 | 99.5 | 76.6 | 16.1 | 92.3 |
| B14 | 1 | 0.4 | 4.5 | 5.9 | 6 | 0.2 | 350 | 99.6 | 79.0 | 14.3 | 92.9 |
| B15 | 1 | 0.4 | 4.5 | 4 | 18 | 0.1 | 350 | 96.3 | 77.3 | 13.9 | 87.8 |
| B16 | 1 | 0.4 | 4.5 | 4 | 2.5 | 0.1 | 350 | 96.6 | 66.9 | 23.6 | 87.6 |
| B17 | 1 | 0.4 | 4.5 | 4 | 12.5 | 1.0 | 350 | 99.2 | 70.8 | 19.3 | 89.3 |

Note: Acetaldehyde, acetic acid, carbon monoxide, and carbon dioxide were additionally yielded as by-products.

EXAMPLES B18 TO B21

A catalyst produced in substantial accordance with Example B4 so as to contain molybdenum, bismuth, iron, cobalt, nickel, boron, and sodium in the atomic ratio of 12 : 1 : 1 : 4 : 4.5 : 0.1 : 0.05 was subjected to varied final baking temperatures by being 29 percent supported on porous α-alumina balls each with a diameter of about 5 millimeters. The reactions of these Examples D18 to D21 with the aforesaid gaseous mixture were conducted as set forth in Example B4. The results are given in Table B-2 below.

Table B-2

| Example No. | Final Temperature, °C | $C_3$ Conversion, % | ACR Selectivity, % | AA Selectivity, % | ACR + AA One-pass Yield, % |
| --- | --- | --- | --- | --- | --- |
| B18 | 500 | 98.0 | 62.5 | 26.8 | 87.6 |
| B19 | 530 | 98.3 | 72.4 | 18.6 | 89.5 |
| B20 | 560 | 97.8 | 73.9 | 13.3 | 85.3 |
| B21 | 590 | 97.0 | 77.8 | 11.2 | 86.3 |

EXAMPLE B5

The powder/produced in substantial accordance with Example B4 and processed up to the mentioned step of thermal decomposition was then formed into a columnar shape with a diameter of about 4 millimeters by

EXAMPLE B22

The catalyst of Examples B18 to B21 B21 was formed into columnar shape with a diameter of about 4 millimeters by the same way as in Example D5 and was baked at about 546° C for 3 hours in air. Twenty milliliters of the catalyst thus processed was subjected to the same reaction as in Examples B18 to B21, except that the reaction temperature was reduced to about 323° C. The results were:
  Propylene conversion = 96.0 percent.
  Acrolein selectivity = 84.9 percent.
  Acrylic acid selectivity = 8.0 percent.
  (AA + ACR) one-pass yield = 89.0 percent.
By-products such as acetaldehyde, acetic acid, carbon monoxide, and carbon dioxide were also produced.

EXAMPLE B23

Thirty milliliters of the catalyst of Example B20 was mixed with 20 milliliters of Rasching rings with an outer diameter of 5 millimeters. The mixture was filled in a pressure-resistant reactor tube with an inner diameter of 16 millimeters, and was subjected to reaction, at a temperature of 390° C and pressure of 3 atmospheric pressures and for a contact time of 9 seconds, with a gaseous mixture consisting of 5 percent by volume of propylene, 40 percent by volume of steam, and 55 percent by volume of air. The results are as follows:
  Propulene conversion = 92.7 percent.
  Acrolein selectivity = 68.4 percent.
  Acrylic acid selectivity = 16.8 percent.
  (AA + ACR) one-pass yield = 85.1 percent.
Acetaldehyde, acetic acid, carbon monoxide, and carbon dioxide were also obtained as by-products.

EXAMPLE B24

The catalyst of Example B1 was processed and subjected to reaction in substantial accordance with Example B23, only with the reaction temperature lowered to 350° C, to obtain the following results:
  Propylene conversion = 96.8 percent.
  Acrolein selectivity = 78.1 percent.
  Acrylic acid selectivity = 13.4 percent.
  (AA + ACR) one-pass yield = 91.5 percent.

EXAMPLE B25

Fifty-three grams of ammonium paramolybdate was dissolved in 75 milliliters of lukewarm water, and 92 grams of silica sol containing 20 percent of silicon dioxide was sufficiently dispersed in the solution. While being agitated sufficiently, this mixture was successively admixed with (1) 12.1 grams of bismuth nitrate [$Bi(NO_3)_3 \cdot 5H_2O$] dissolved in 1.2 milliliters of concentrated nitric acid and 9 milliliters of distilled water, (2) 43.7 grams of cobalt nitrate [$Co(NO_3)_2 \cdot 6H_2O$] dissolved in 60 milliliters of distilled water, (3) 18.2 grams of nickel nitrate [$Ni(NO_3)_2 \cdot 6H_2O$], (4) 4 grams of ferric nitrate [$Fe(NO_3)_3 \cdot 9H_2O$], (5) 1.1 grams of stannous chloride ($SnCl_2 \cdot 2H_2O$), and (6) 0.24 grams of borax ($Na_2B_4O_7 \cdot 10H_2O$). The precipitates formed in the resultant solution were evaporated to dryness, pulverized, and thermally decomposed into oxide by means of an electric furnace heated to about 350° C for a one-hour period. A small quantity of water was added to 17.1 grams of the powder thus formed, and the wet powder was sufficiently milled in a kneading machine. The product, carried by/40 grams of porous α-alumina (of Fujimi Kenmazai Kogyo K.K.), was baked at about 520° C for 3 hours in air. The resultant silicon boron sodium, and tior in the atomic ratio of 12 : 1 : 0.4 : 6 : 25 : 0.4 : 12.5 : 0.1 : 0.05 : 0.2 catalyst proved to contain molybdenum, bismuth, cobalt, nickel, iron.

Twenty milliliters of the thus-produced catalyst was filled in a reactor tube with an inner diameter of 15.0 millimeters and was subjected to reaction, at a temperature of about 320° C and for a contact time of 9 seconds, with a gaseous mixture consisting of 4.5 percent by vol. of propylene, 53 percent by vol. of air, and 42.5 percent by vol. of steam. What follows is the results:
  propylene conversion = 95.8 percent
  Acrolein selectivity = 86.4 percent
  Acrylic acid selectivity = 8.6 percent.
  (AA + ACR) one-pass yield = 91.1 percent.
Acetaldehyde, acetic acid, carbon monoxide, and carbon dioxide were also produced a little.

EXAMPLE B26

The catalyst of Example B25 was subjected to the reaction set forth in Example B23, only with the reaction temperature lowered to about 350° C. The following results were obtained:
  Propylene conversion = 96.6 percent.
  Acrolein selectivity = 80.4 percent.
  Acrylic acid selectivity = 13.6 percent.
  (AA + ACR) one-pass yield = 90.3 percent.

EXAMPLES B27 TO B32

Catalysts of varied compositions within the scope of this invention were prepared in substantial accordance with Example D25 and were further subjected to the same reaction at different temperatures, with the results set forth in the following Table D-3:

Table B-3

| Example No. | Catalyst Composition | | | | | | Borax (as "B") | Reaction Temperature, °C | $C_3$ Conversion % | ACR Selectivity, % | AA Selectivity, % | ACR + AA One-pass Yield, % |
| --- | --- | --- | --- | --- | --- | --- | --- | --- | --- | --- | --- | --- |
| | Bi | Fe | Ni | Co | Sn | Si | | | | | | |
| B27 | 1 | 1 | 4.5 | 4 | 0.2 | 12.5 | 0.1 | 320 | 96.1 | 85.1 | 6.9 | 88.3 |
| B28 | 1 | 0.4 | 4.5 | 4 | 0.2 | 6.25 | 0.1 | 320 | 94.0 | 83.9 | 8.7 | 86.9 |
| B29 | 1 | 0.4 | — | 8 | 0.2 | 12.5 | 0.1 | 350 | 93.4 | 95.1 | 9.0 | 87.8 |
| B30 | 2 | 0.4 | — | 8 | 0.2 | 12.5 | 0.1 | 350 | 93.9 | 85.6 | 8.9 | 88.7 |
| B31 | 1 | 0.4 | 4 | — | 0.2 | 6.25 | 0.1 | 320 | 92.5 | 86.9 | 5.3 | 85.3 |
| B32 | 1 | 1 | — | 8 | 0.2 | 12.5 | 0.1 | 320 | 93.6 | 84.3 | 6.0 | 84.5 |

Note : By-products such as acetaldehyde, acetic acid, carbon monoxide, and carbon dioxide were also produced.

EXAMPLE B33

A catalyst was prepared in substantial accordance with Example Br, only with the borax substituted with 01. grams of the compound $MnB_4O_7 \cdot 8H_2O$ and was subjected to the same reaction under the same conditions. The results were as follows:
  Propylene conversion = 9819 percent.
  Acrolein selectivity = 77.7 percent.
  Acrylic acid selectivity = 14.0 percent.
  (AA + ACR) one-pass yield = 90.7 percent.
Acetaldehyde, acetic acid, carbon monoxide, and carbon dioxide were also produced a little.

COMPARISON B1

A catalyst was prepared by removing the silica content from the catalyst of Example Dr, and was subjected to the same reaction as that set forth in the same Example. The results are given below:
Propylene conversion = 27.4 percent.
Acrolein selectivity = 87.9 percent.
Acrylic acid selectivity = 11.0 percent.
(AA + ACR) one-pass yield = 27.1 percent.
The by-production of acetaldehyde, acetic acid, carbon monoxide, and carbon dioxide also resulted.

COMPARISON B2

A catalyst was prepared in substantial accordance with Example Br, only in such a manner that the Fe content alone of the catalyst was increased to 3, which is out of the scope of this invention. This catalyst was subjected to the ame reaction as that set forth in Example B4, to obtain the results given below:
Propylene conversion = 81.4 percent.
Acrolein selectivity = 70.2 percent.
Acrylic acid selectivity = 4.6 percent.
(AA + ACR) one-pass yield = 60.9 percent.
Acetaldehyde, acetic acid, carbon monoxide, and carbon dioxide were produced a little.

COMPARISON B3

A catalyst was prepared which had a composition exactly equivalent to that set forth in Examples B18 to B21 except fot the absence of bismuth. This catalyst was subjected to the same reaction as in the preceding Comparison B2, with the results given below:
Propylene conversion = 5.9 percent.
Acrolein selectivity = 17.4 percent.
Acrylic acid selectivity = 7.4 percent.
(AA 30 ACR) one-pass yield = 1.t percent.
Acetaldehyde, acetic acid, carbon monoxide, and carbon dioxide were produced a little.

COMPARISON B4

A catalyst without any Fe content, prepared like the catalyst of Comparison B1 in other details, was subjected to the same reaction, with the results given below:
Propylene conversion = 1.9 percent.
Acrolein selectivity = 77.4 percent.
Acrylicacid selectivity = 0 percent.
(AA + ACR) one-pass yield 1.5 percent.

EXAMPLE B34

A catalyst was prepared in substantial accordance with Example B1, except that (1) the second solution was formed by dissolving 12.1 grams of bismuth nitrate in a solution of 1.2 milliliters of concentrated nitric acid and 9 milliliters of distilled water; (2) the second solution to be dissolved in the solution was formed by 29.1 grams of cobalt nitrate, 32.7 grams of nickel nitrate, 4 grams of ferric nitrate, 0.21 gram of sodium nitrate ($NaNO_3$), and 70 milliliters of distilled water; (3) 0.48 gram of sodium tetraborate was used for the third solution; and (4) the milled mixture of oxides was 28.8 percent supported by the $\alpha$-alumina carrier. The catalyst thus prepared proved to contain mulybdenum, bismuth, iron, cobalt, nickel, silicon, boron, and sodium in the atomic ratio of 12 : 1 : 0.4 : 4 : 4.5 : 6.3 : 0.2 : 0.2. This catalyst was subjected to the same reaction as that in the same Example B1. The results were as follows:
Propylene conversion = 99.7 percent.
Acrolein selectivity = 79.8 percent.
Acrylic acid selectivity = 14.8 percent.
(AA + ACR) one-pass yield = 94.3 percent.

EXAMPLE B35

The 0.24 grams of sodium tetraborate in Example B1 was substituted with 0.69 grams of sodium metaborate ($NaBO_2 \cdot 4H_2O$) to prepare a catalyst in exact accordance with the same Example in other details. This catalyst was further subjected to the same reaction as that in Example B1, with the results:
Propylene conversion = 99.5 percent.
Acrolein selectivity = 81.2 percent.
Acrylic acid selectivity = 13.4 percent.
(AA + ACR) one-pass yield = 94.1 percent.

EXAMPLE C1

To 9.4 grams of finely granulated silica (a commercially available product known by the trade name "Carplex," of Shionogi Seiyaku K.K., of Japan) was added 53 grams of ammonium parabolydate [$(NH_4)_6Mo_7O_{24} \cdot 4H_2O$] dissolved in 75 milliliters of likewarm water, thereby to provide a first solution.

A second solution was prepared by dissolving the following compounds in 70 milliliters of distilled water containing 8 milliliters of nitric acid: 60.5 grams of bismuth nitrate[$Bi(NO_3)_3 \cdot 5H_2O$], 29.1 grams of nickel nitrate [$Ni(NO_3)_2 \cdot 6H_2O$], 4.0 grams of ferric nitrate [$Fe(NO_3)_3 \cdot 9H_2O$], and 1.1 grams of stannous chloride ($SnCl_2 \cdot 2H_2O$). This second solution was mixed with the first solution.

Further to this mixed solution was added 0.24 gram of borax ($Na_2B_4O_7 \cdot 10H_2O$) dissolved in 10 milliliters of distilled water. The precipitates formed in the resultant solution were evaporated to dryness while being stirred. The thus-formed cake was subjected to thermal decomposition at about 300° C for one hour in an electric furnace. Added with a small quantity of water, 21.5 grams of the above obtained mixture of oxides was sufficiently milled in a kneading machine and was then made to be carried on 40 grams of $\alpha$-alumina in the form of porous balls each with a diameter of 5 millimeters (the product of Fujimi Kenmazai Kogyo K.K.). The oxides were baked in an electric furnace at about 550° C for 3 hours. The which constituted 31.6 percent by weight of the total product, catalyst thus prepared, /proved to contain molybdenum, bismuth, iron, nickel, tin, silicon, boron, and sodium in the atomic ratio of 12 : 5 : 0.4 : 4 : 0.2 : 6.3 : 0.1 : 0.05.

Twenty milliliters of this catalyst was filled in a reactor tube of stainless steel with an inner diameter of 15 millimeters, and was subjected to reaction, at a temperature of 350° C and for a contact time of 9 seconds, with a gaseous mixture consisting of 4.5 percent by volume of propylene, 53.0 percent by volume of air, and 42.5 percent by volume of steam. The following results were obtained:
Propylene conversion = 95.6 percent.
Acrolein selectivity = 82.5 percent
Acrylic acid selectivity = 10.t percent.
(AA + ACR) one-pass yield = 88.9 percent.
Acetaldehyde, acetic acid, carbon monoxide, and carbon dioxide were produced.

The results of the same reaction of this catalyst with the above specified gaseous mixture, in which only the temperature was varied to 320° C and 380° C, are given in the following Table C-1 by way of comparison:

Table C-1

| Reaction Temperature, °C | C₃ Conversion, % | ACR Selectivity, % | AA selectivity, % | ACR + AA One-pass Yield, % |
| --- | --- | --- | --- | --- |
| 320 | 84.8 | 88.8 | 5.6 | 80.8 |
| 350 | 95.6 | 82.5 | 10.5 | 88.9 |
| 380 | 98.6 | 72.9 | 16.3 | 88.0 |

EXAMPLES C2 TO C4

Three catalysts were prepared in substantial accordance with Example C1, except that the final calcining temperature was varied to 500°, 520°, and 580° C, respectively. The results of the reactions between these catalysts and the gaseous mixture, conducted as described in Example C1, are summarized in the following Table C-2:

Table E2

| Example No. | Final Firing Temperature, °C | Reaction Temperature, °C | C₃ Conversion % | ACR Selectivity, % | AA Selectivity, % | ACR+AA One-pass Yield, % |
| --- | --- | --- | --- | --- | --- | --- |
| E2 | 520 | 350 | 94.0 | 80.8 | 9.5 | 84.9 |
|    |     | 380 | 97.2 | 72.7 | 15.6 | 85.8 |
| E3 | 500 | 350 | 94.8 | 78.4 | 10.7 | 84.5 |
|    |     | 380 | 98.6 | 67.2 | 17.4 | 83.4 |
| E4 | 580 | 350 | 93.3 | 81.3 | 8.9 | 84.2 |

EXAMPLE C5

The cake obtained through the procedure set forth in Example C1 was decomposed at a temperature (hereinafter referred to as a "decomposition temperature") of about 350° C. Admixed with a small quantity of distilled water, 11.9 grams of the thus-formed mixture of oxides was sufficiently wet-milled and was made to be carried on 40 grams of α-alumina in the form of porous balls with a diameter of 5 millimeters (the product of Fujimi Kenmazai Kogyo K.K.). The oxides thus supported on the carrier were ca;comed at about 500° C for 3 hours in an electric furnace. The catalyst prepared in this manner constituted 20.6 percent by weight of the total product.

This catalyst was subjected to the same reaction as that set forth in Example C1, with the reaction temperature set to 350° and 380° C. The results were as follows:

| Reaction Temperature, °C | C₃ Conversion, % | ACR Selectivity, % | AA Selectivity, % | ACR + AA One-pass Yield, % |
| --- | --- | --- | --- | --- |
| 350 | 90.8 | 81.3 | 9.3 | 823 |
| 380 | 95.4 | 71.3 | 15.2 | 825 |

EXAMPLE C6

A catalyst containing molybdenum, bismuth, iron, cobalt, tin, silicon, boron, and sodium in the atomic ratio of 12 : 5 : 0.4 : 4 : 0.2 : 6.2 : 0.1 : 0.05 was prepared in substantial accordance with Example E1, only the nickel content of the catalyst of Example E1 being substituted with cobalt in the catalyst of this Example C6. This latter catalyst was subjected to the same reaction as that of Example C1, providing the results tabulated in the following:

Table C4

| Reaction Temperature, °C | C₃ Conversion, % | ACR Selectivity, % | AA Selectivity, % | ACR + AA One-pass Yield, % |
| --- | --- | --- | --- | --- |
| 350 | 88.7 | 83.7 | 7.5 | 80.9 |
| 380 | 97.1 | 74.0 | 13.8 | 85.3 |

EXAMPLES C7 to C22

Catalysts containing molybdenum, bismuth, iron, cobalt, nickel, tin, boron, and silicon in varied atomic ratios, as set forth in the following Table E-5, were prepared and subjected to the reaction in substantial accordance with Example C1. (The catalysts were from 25 to 30% supported on the α-alumina carrier.)

Table C-5

| Example No. | Bi | Fe | Co | Ni | Sn | B | Si | Reaction Temperature, °C | C₃Conversion, % | ACR Selectivity, % | AA Selectivity, % | ACR+AA One-pass Yield, % |
| --- | --- | --- | --- | --- | --- | --- | --- | --- | --- | --- | --- | --- |
| C 7 | 4 | 0.4 | — | 5.5 | 0.2 | 0.1 | 6.3 | 350 | 98.1 | 70.7 | 15.7 | 84.8 |
| C 8 | 6 | 0.4 | — | 4 | 0.2 | 0.1 | 6.3 | 350 | 94.8 | 76.4 | 10.4 | 823 |
| C 9 | 5.5 | 0.3 | 3.5 | — | 0.2 | 0.1 | 12.5 | 350 | 90.6 | 81.3 | 9.0 | 81.8 |
| C10 | 5 | 1 | — | 4 | 0.2 | 0.1 | 6.25 | 350 | 97.5 | 78.6 | 11.5 | 87.8 |

Table C-5-continued

| Example No. | Catalyst Composition | | | | | | | Reaction Temperature, °C | C₃ Conversion, % | ACR Selectivity, % | AA Selectivity, % | ACR+AA One-pass Yield, % |
|---|---|---|---|---|---|---|---|---|---|---|---|---|
| | Bi | Fe | Co | Ni | Sn | B | Si | | | | | |
| | | | | | | | | 320 | 90.8 | 86.9 | 6.1 | 84.4 |
| C11 | 5 | 2 | 1.5 | — | 0.2 | — | 12.5 | 380 | 88.7 | 82.1 | 12.2 | 83.6 |
| C12 | 5 | 2 | — | 4 | 0.2 | 0.1 | 6.3 | 350 | 99.4 | 76.1 | 6.6 | 82.2 |
| | | | | | | | | 320 | 94.9 | 82.5 | 4.6 | 82.7 |
| C13 | 5 | 6 | — | 4 | 0.2 | 0.1 | 12.5 | 350 | 95.4 | 76.9 | 8.2 | 81.3 |
| C14 | 5 | 0.4 | 6 | — | 0.2 | 0.1 | 12.5 | 380 | 95.1 | 74.5 | 12.9 | 83.1 |
| C15 | 5 | 0.4 | 2 | — | 0.2 | 0.1 | 6.3 | 350 | 91.4 | 83.0 | 9.7 | 84.7 |
| C16 | 5 | 0.4 | — | 6 | 0.2 | 0.1 | 6.3 | 350 | 91.1 | 76.4 | 8.3 | 77.2 |
| C17 | 5 | 0.4 | — | 2 | 0.2 | 0.1 | 6.3 | 350 | 96.6 | 66.4 | 15.8 | 79.4 |
| C18 | 4.5 | 0.4 | 3 | 3.5 | 0.2 | 0.1 | 6.3 | 380 | 96.6 | 73.1 | 15.3 | 85.4 |
| C19 | 5 | 0.4 | — | 4 | 0.5 | 0.1 | 6.3 | 350 | 98.1 | 71.4 | 15.1 | 84.9 |
| C20 | 5 | 0.4 | — | 4 | 0.5 | 0.1 | 12.5 | 350 | 97.2 | 66.6 | 23.7 | 87.7 |
| C21 | 5 | 0.4 | — | 4 | 1 | 0.1 | 12.5 | 350 | 93.0 | 69.6 | 19.7 | 83.0 |
| C22 | 5 | 0.4 | — | 4 | 0.2 | 1 | 6.3 | 350 | 99.2 | 69.1 | 14.9 | 83.3 |

EXAMPLE C23

To 18.8 grams of finely granulated silica was added 53 grams of ammonium paramolybdate [$(NH_4)_6Mo_7O_{24}\cdot 4H_2O$] dissolved in 75 milliliters of likewarm water. This solution was admixed with another solution which was formed by dissolving the following compounds in 70 milliliters of distilled water containing 8 milliliters of nitric acid: 54.5 grams of bismuth nitrate [$Bi(NO_3)_3\cdot 5H_2O$], 29.1 grams of nickel nitrate [$Ni(NO_3)_2\cdot 6H_2O$], 4.0 grams of ferric nitrate [$Fe(NO_3)_3\cdot 9H_2O$], and 1.1 grams of stannous chloride ($SnCl_2\cdot 2H_2O$). The resultant admixture was further admixed with 0.24 gram of borax ($Na_2B_4O_7\cdot 10H_2O$) dissolved in 10 milliliters of distilled water. While being agitated, the precipitates formed in the thus-obtained solution were evaporated to dryness, and the cake so produced was subjected to decomposition at 300° C for one hour in an electric furnace. The resultantly produced mixture of oxides was admixed with graphite in the weight ratio of 100 to 1. Upon being well intermingled, the admixture was tabletted into a columnar shape with a diameter of about 4 millimeters. This was further calcined at 500° C for 3 hours in an electric furnace.

The catalyst prepared in this manner proved to contain molybdenum, bismuth, iron, nickel, tin, silicon, boron, and sodium in the atomic ratio of 12 : 4.5 : 0.4 : 4 : 0.2 : 12.5 : 0.1 : 0.05. This catalyst, when subjected to the same reaction as that set forth in Example C1, exhibited the results of Table C-6 below.

Table C-6

| Reaction Temperature, °C | C₃ Conversion, % | ACR Selectivity, % | AA Selectivity, % | ACR + AA One-pass Yield, % |
|---|---|---|---|---|
| 320 | 96.0 | 73.2 | 13.1 | 83.0 |
| 350 | 100 | 58.8 | 23.2 | 82.0 |

EXAMPLES C24 TO C26

The Si content of the catalyst of Example C23 was varied to provide three modifications of the catalyst, which were subjected to the same reaction as in Example C23. The results are given in Table C-7.

Table C-7

| Example No. | Si Content (in atomic ratio to Mo=12) | Reaction Temperature, °C | C₃ Conversion, % | ACR Selectivity, % | AA Selectivity, % | ACR + AA One-pass Yield, % |
|---|---|---|---|---|---|---|
| C24 | 15 | 320 | 97.3 | 70.6 | 13.9 | 82.3 |
| C25 | 20 | 320 | 97.7 | 70.0 | 15.0 | 83.0 |
| C26 | 30 | 320 | 97.5 | 74.2 | 11.3 | 83.4 |

EXAMPLE C27

Five milliliters of the/catalyst of Example E2 was charged into a reactor tube of stainless steel with an inner diameter of 15 millimeters, and was subjected to reaction, at a temperature of about 400° C and for a contact time of 2.5 seconds, with a gaseous mixture consisting of 6.6 percent by vol. of steam. The results were as follows:

Propylene conversion = 62.9 percent.
Propylene conversion = 62.9 percent.
Acrolein selectivity = 82.9 percent.
Acrylic acid selectivity = 6.1 percent.
(AA + ACR) one-pass yield 2 56.0 percent.
Acetaldehyde, acetic acid, carbon monoxide, and carbon dioxide were also byproduced.

EXAMPLE C28

A catalyst was prepared in substantial accordance with Example C1, only with the mentioned "Carplex" substituted with "Aerosil 200" (a trade name given to silica manufactured by Nippon Aerosil K.K., of Japan). (This Example was 27.9 percent supported on the α-alumina carrier in the process of catalyst production.) The catalyst was further subjected to the same reaction/as in Example C1 at varied temperatures, with the results shown in the following Table C-8:

Table C-8

| Reaction Temperature, °C | $C_3$ Conversion, % | ACR Selectivity, % | AA Selectivity, % | ACR + AA One-pass Yield, % |
| --- | --- | --- | --- | --- |
| 320 | 86.9 | 89.5 | 4.4 | 81.6 |
| 350 | 96.4 | 83.3 | 8.4 | .88.4 |
| 380 | 98.7 | 74/7 | 14.2 | 87.7 |

COMPARISON C1

The bismuth content in this example is out of the scope of this invention. The 60.5 grams of bismuth nitrate [$Bi(NO_3)_3.5H_2O$] and 8 milliliters of nitric acid in Example E1 were substituted, respectively, with 96.8 grams of the former and 13 milliliters of the latter to provide a catalyst containing molybdenum, bismuth, iron, nickel, tin, silicon, boron, and sodium in the atomic ration of 12 : 8 : 0.4 : 4 : 0.2 : 6.3 : 0.1 : 0.05. The reaction of this catalyst with the gaseous mixture in accordance with Example E1 produced the results shown in Table E-9.

COMPARISONS C2 to C7

Several catalysts, the compositions of which are out of the scope of this invention, were prepared and subjected to reaction in substantial accordance with Example C1. The results are also given in Table C-9.

was tabletted and then baked at about 500° C for 6 hours in air. The catalyst thus prepared proved to contain Mo, Bi, Fe, Co, Ni, Si, P, and K in the atomic ratio of 12 : 1 : 2 : 3 : 1 : 9.4 : 2 : 0.2.

Thirty-five milliliters of the catalyst was charged into a reactor tube of stainless steel with an inner diameter of 15 millimeters, and was made to react, at a temperature of 350° C and a contact time of 3.2 seconds, with a gaseous mixture consisting of 4.5 percent by capacity of propylene, 53 percent by capacity of air, and 42.5 per cent by capacity of vapor. The results are summarized below:

Propylene conversion = 88.9 percent.
Acrolein selectivity = 75.8 percent.
Acrylic acid selectivity 14.8 percent.
(AA + ACR) one-pass yield = 80.6 percent.
Acetaldehyde, acetic acid, carbon monoxide, and carbon dioxide were also produced.

Table C-9

| Comparison No. | Catalyst Composition | | | | | | | Reaction Temperature, °C | $C_3$ Conversion, % | ACR Selectivity, T | AA Selectivity, % | ACR+AA One-pass Yield, % |
| --- | --- | --- | --- | --- | --- | --- | --- | --- | --- | --- | --- | --- |
| | Bi | Fe | Co | Ni | Sn | B | Si | | | | | |
| C2 | 8 | 0.4 | — | 4 | 0.2 | 0.1 | 6.3 | 350 | 54.2 | 86.4 | 4.3 | 49.2 |
| C3 | 5 | 0.4 | — | 11 | 0.2 | 0.1 | 6.3 | 350 | 40.4 | 64.0 | 8.6 | 29.3 |
| C4 | 5 | 0.4 | — | — | 0.2 | 0.1 | 12.5 | 350 | 7.8 | 69.0 | 10.9 | 6.2 |
| C5 | 5 | 0.4 | — | 4 | 2 | 0.1 | 6.3 | 380 | 84.8 | 65.0 | 19.2 | 71.4 |
| C6 | 5 | 0.4 | — | 4 | 3 | 0.1 | 12.5 | 350 | 81.4 | 68.4 | 14.7 | 67.6 |
| C7 | 5 | 0.4 | — | 4 | 0.2 | 3 | 12.5 | 350 | 64.1 | 75.2 | 16.2 | 58.6 |

COMPARISON D

Several experiments hereinafter described are to prove the adequacy of the combination of boric acid and sodium, and that of phosphoric acid and potassium.

EXPERIMENT 1

A solution formed by dissolving 63.6 grams of ammonium paramolydate [$(NH_4)_6Mo_7O_{24}.4H_2O$] in 64 milliliters of distilled water was mixed with a solution formed by dissolving 6.9 grams of phosphoric acid (85%) and 0.67 gram of potassium nitrate in 5 milliliters of distilled water. Solution A was thus prepared.

Separately, 8.7 grams of nickel nitrate was dissolved in 5 milliliters of distilled water; 26.2 grams of cobalt nitrate in 10 milliliters of distilled water; 24.2 grams of ferric nitrate in 8 milliliters of distilled water; and 14.5 grams of bismuth nitrate in 10 milliliters of distilled water which had been rendered acidic by the addition of 3 milliliters of concentrated nitric acid. The solutions of these four nitrages were intermingled form Solution B.

This solution B was poured into Solution A while the latter was being agitated. The slurried suspension thus formed was further admixed with 17 grams of silica sol ("Showtex N") as $Si)_2$. The product was evaporated to dryness, further heated to a high temperature, and, upon cooling, pulverized into a powder. This powder

EXPERIMENT 2

The 6.9 grams of phosphoric acid in Experiment 1 was substituted with 4.4 grams of boric acid to prepare a catalyst in exact accordance with the same Experiment in other details. The catalyst proved to contain No, Bi, Fe, Co, Ni, B, K, and Si in the atomic ratio of 12 : 1 : 2 : 3 : 1 : 2 : 0.2 : 9.4.

When subjected to the same reaction as that set forth in Experiment 1 above, this catalyst exhibited the following results:

Propylene conversion = 52.9 percent.
Acrolein selectivity = 90.6 percent.
Acrylic acid selectivity = 5.5 percent.
(AA + ACR) one-pass yield = 50.8 percent.
Secondary products such as acetaldehyde, acetic acid, carbon monoxide, and carbon dioxide were also yielded.

EXPERIMENT 3

The 0.67 gram of potassium nitrate in Experiment 2 was substituted with 0.5 gram of sodium nitrate to prepare a catalyst in exact accordance with Experiment 2 in other details. The thus-prepared catalyst proved to contain Mo, Ni, Fe, Co, Ni, B, Na, and Si in the atomic ratio of 12 : 1 : 2 : 3 : 1 : 2 : 0.2 : 9.4.

This catalyst was subjected to the reaction explained in Experiment 1, with the results given in the following:

Propylene conversion = 80.4 percent.
Acrolein selectivity = 81.5 percent.

Acrylic acid selectivity = 11.3 percent.
(AA + ACR) one-pass yield = 74.6 percent.
Acetaldehyde, acetic acid, carbon monoxide, and carbon dioxide were additionally yielded as secondary products.

EXPERIMENT 4

This Experiment is to demonstrate the fact that, while the catalyst of Experiment 3 is inferior to that of Experiment 1 in activity and in the yield of acrolein and acrylic acid, the former catalyst can exhibit better results if its B and Na contents are modified.

The 4.4 grams of boric acid and 0.5 grams of borax ($Na_2B_4O_7 \cdot 10H_2O$) dissolved in 10 milliliters of distilled water to provide a catalyst in exact conformity with Experiment/3 in other details. This catalyst, containing Mo, Bi, Fe, Co, Ni, B, Na, and/Si in the atomic ratio of 12 : 1 : 2 : 3 : 1 : 0.4 : 0.2 : 9.4, was subjected to the same reaction as that in Experiment 1. The results were as follows:
Propylene conversion = 89.2 percent.
Acrolein selectivity = 81.5 percent.
Acrylic acid selectivity = 11.7 percent.
(AA + ACR) one-pass yield = 83.1 percent.
Acetaldehyde, acetic acid, carbon monoxide, and carbon dioxide were also produced secondarily.

EXPERIMENT 5

The 0.67 gram of potassium nitrate in Experiment 1 was substituted with 0.5 gram of sodium nitrate to prepare a catalyst in exact accordance with the same Experiment in other details. This catalyst contained Mo, Bi, Fe, Co, Ni, P, Na, and Si in the atomic ratio of 12 : 1 : 2 : 3 : 1 : 2 : 0.2 : 9.4.

The results of the reaction of this catalyst with the gaseous mixture as set forth in Experiment 1 were as follows:
Propylene conversion = 65.2 percent.
Acrolein selectivity = 80.8 percent.
Acrylic acid selectivity = 11.4 percent.
(AA + ACR) one-pass yield = 60.1 percent. Acetaldehyde, acetic acid, carbon monoxide, and carbon dioxide were further produced secondarily.

The results given in Experiments 1 to 5 are summarized in Table F-1.

Table D-1

| Experiment No. | X | Y | Reaction Temperature, °C | Contact Time, sec | $C_3$ Conversion, % | ACR Selectivity, % | AA Selectivity, % | ACR+AA One-pass Yield, % |
|---|---|---|---|---|---|---|---|---|
| 1 | P 2 | K 0.2 | 350 | 3.2 | 88.9 | 75.8 | 14.8 | 80.6 |
| 2 | B 2 | K 0.2 | 350 | 3.2 | 52.9 | 90.6 | 5.5 | 50.8 |
| 3 | B 2 | Na 0.2 | 350 | 3.2 | 80.4 | 81.5 | 11.3 | 74.6 |
| 4 | B 0.4 | Na 0.2 | 350 | 3.2 | 89.2 | 81.5 | 11.7 | 83.1 |
| 5 | P 2 | Na 0.2 | 350 | 3.2 | 65.2 | 80.8 | 11.4 | 60.1 |

EXPERIMENTS 6 TO 8

Catalysts each supported about/30 percent by the porous α-alumina carrier (of Fujimi Kenmazai Kogyo K.K.), as set forth in Example D1, were subjected to the same reaction for a contact time of 9 seconds. The results are summarized in Table D-2.

Table D-2

| Experiment No. | Catalyst Composition Mo-Bi-Fe-Co-Ni-Si | | Reaction Temperature, °C | $C_3$ Conversion, % | ACR Selectivity, % | AA Selectivity, % | Aa + ACR One-pass Yield, % |
|---|---|---|---|---|---|---|---|
| 6 | 12 1 2 3 1  9.4 | P 2  K 0.2 | 350 | 90.4 | 83.5 | 7.2 | 82.9 |
| 7 | " | B 2  K 0.2 | · | 66.7 | 86.4 | 6.9 | 62.2 |
| 8 | " | B 0.4  K 0.2 | 350 | 57.9 | 90.4 | 2.3 | 53.7 |

Note: Acetaldehyde, acetic acid, carbon moboxide, and carbon dioxide were also produced secondarily.

EXPERIMENTS 9 TO 11

In Experiments 1 to 8, the catalysts containing Mo, Bi, Fe, Co, Ni, and Si in the atomic ratio of 12 : 1 : 2 : 3 : 1 : 9.4 were additionally provided with P, B, K, and Na contents/indifferent combinations, to demonstrate the results that the combinations of P and K and of B and Na are advantageous while the combinations of P and Na and of B and K are not. The present Experiments 9 and 10 were conducted to prove the fact that even when the different combinations of P, K, B, and Na are added to catalysts containing Mo, Bi, Fe, Co, Ni, and Si in the atomic ratio of 12 : 1 : 0.4 : 4 : : 4.5 : 6.3 or thereabouts, the combinations of B and Na and of P and K are favorable, while the combination of B and K leads to no satisfactory yield, as shown in the following Table D-3, in which the catalysts were prepared in substantial accordance with Example B1:

Table D-3

| Experiment No. | Catalyst Composition Mo-Bi-Fe-Co-Ni-Si | P-K / P Na / B K / B Na | Amount Carried, % | C₃ Conversion % | ACR Selectivity, % | AA Selectivity, % | AA + ACR One-pass Yield, % |
|---|---|---|---|---|---|---|---|
| 9 | 12-1-0.4-4-4.5-6.3 | P-K 0.07–0.2 (K₃PO₄) | 29.9 | 96.8 | 84.3 | 8.5 | 89.8 |
| 10 | " | P Na 0.07–0.2 (Na₃PO₄) | 31.0 | 82.7 | 84.8 | 7.7 | 76.5 |
| 11 | 12-1-0.4-4.7-5-7- | B K 0.2–0.2 | 23.7 | 78.8 | 89.9 | 2.9 | 73.1 |
|  | 12-1-0.4:4:4.5:6.3- | B Na 0.1–0.05 | 22.0 | 97.5 | 84.6 | 10.8 | 93.0 |

Although the process of this invention has been described very specifically in the foregoing in terms of Examples thereof, many modifications thereof will readily occur to those skilled in the art. It is therefore appropriate that the appended claims be construed broadly and in a manner consistent with the principles and scope of the invention herein disclosed.

We claim:

1. A process for producing acrolein by vaporphase catalytic oxidation of propylene with molecular oxygen, which comprises oxidizing propylene with molecular oxygen at a temperature of 240° to 450° at a pressure of 0.5 to 10 atmospheres of pressure over a catalyst of a composition represented by the formula $$Mo_a Bi_b Co_c Ni_d Fe_e O_f B_g Na_h Si_j,$$

the boron having been introduced in the catalyst in the form of a sodium borate and the subscript characters $a$ through $j$ designate the respective numbers of atoms are as follows:
$a = 12$
$b = 0.1$ to $10$
$c = 0$ to $10$
$d = 0$ to $10$
$c + d = 0.1$ to $15$
$e = 0.05$ to $8$
$f = 25$ to $120$
$g = 0.01$ to $2$
$h = 0.01$ to $2$
$g + h = 0.02$ to $4$
$j = 0$ to $40$.

2. A process according to claim 1, wherein the propylene is present in a concentration of 2 to 10 mol percent and the oxygen is present in a concentration of 5 to 30 mol percent.

3. A process according to claim 1 in which the catalyst is a composition representable by the formula

$$Mo_a Bi_b Co_c Ni_d Fe_e O_f B_g Na_h$$

wherein the subscript characters $a$ through $h$ designate respective numbers of atoms are as follows:
$a = 12$
$b = 4$ to $7$
$c = 0$ to $10$
$d = 0$ to $10$
$c + d = 0.1$ to $10$
$e = 0.05$ to $0.5$
$f = 25$ to $80$
$g = 0.01$ to $2$
$h = 0.10$ to $2$ 4. A process according to claim 1 in which said catalyst of the composition is supported on a carrier selected from the group consisting of silicon carbide and α-alumina.

5. A process according to claim 1 in which the subscript characters $a$ through $j$, are as follows:
$a = 12$
$0.1 \leq b \leq 4$
$c = 0$ to $10$
$d = 0$ to $10$
$c + d = 1$ to $15$
$e = 0.1$ to $2.5$
$f = 30$ to $120$
$g = 0.01$ to $2$
$h = 0.01$ to $2$
$g + h = 0.02$ to $4$
$j = 0.5$ to $40$ 6. A process according to claim 5 in which the subscript characters $a$ through $j$, are as follows:
$a = 12$
$0.1 \leq b \leq 4$
$c = 0$ to $2$
$d = 0$ to $2$
$1 \leq (c + d) \, 2$
$0.1 < e < 0.5$
$f = 30$ to $120$
$g = 0.01$ to $2$
$h = 0.01$ to $2$
$g + h = 0.02$ to $4$
$j = 0.5$ to $40$ 7. A process according to claim 5 in which the subscript characters $a$ through $j$, are as follows:
$a = 12$
$0.1 \leq b \leq 4$
$c = 0$ to $10$
$d = 0$ to $10$
$c + d = 2$ to $15$
$0.1 \leq e < 0.5$
$f = 30$ to $120$
$g = 0.01$ to $2$
$h = 0.01$ to $2$
$g + h = 0.02$ to $4$
$j = 0.5$ to $40$ 8. A process according to claim 5 in which the subscript characters $a$ through $j$, are as follows:
$a = 12$
$0.1 \leq b < 4$
$c = 0$ to $10$
$d = 0$ to $10$
$c + d = 1$ to $15$
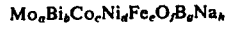
$e = 0.5$ to $2.5$
$f = 30$ to $120$
$g = 0.01$ to $2$
$h = 0.01 - 2$
$g + h = 0.02$ to $4$ $j = 0.5$ to $40$ 9. A process according to claim 5 in which the boron and sodium are supplied in combination in the form of a borate.

10. A process according to claim 5 in which the catalyst of the composition is supported on a carrier selected from the group consisting of silicon carbide and $\alpha$-alumina.

* * * * *